US008251910B2

(12) United States Patent
Saito et al.

(10) Patent No.: US 8,251,910 B2
(45) Date of Patent: Aug. 28, 2012

(54) APPARATUS FOR MEASURING VASCULAR VISCOELASTICITY INDEX

(75) Inventors: Yukiyoshi Saito, Tokyo (JP); Minoru Tokiwa, Tokyo (JP); Toshikazu Yokokawa, Tokyo (JP); Takashi Yokoi, Tsukuba (JP); Hidehiko Komine, Tsukuba (JP); Yoshiyuki Asai, Tsukuba (JP)

(73) Assignees: Shisei Datum Co., Ltd., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 701 days.

(21) Appl. No.: 12/309,843

(22) PCT Filed: Jul. 7, 2007

(86) PCT No.: PCT/JP2007/065207
§ 371 (c)(1),
(2), (4) Date: Jul. 27, 2009

(87) PCT Pub. No.: WO2008/016125
PCT Pub. Date: Feb. 7, 2008

(65) Prior Publication Data
US 2009/0306523 A1 Dec. 10, 2009

(30) Foreign Application Priority Data
Jul. 31, 2006 (JP) .................................. 2006-208030

(51) Int. Cl.
*A61B 5/02* (2006.01)
(52) U.S. Cl. ....................................................... 600/481
(58) Field of Classification Search .................. 600/481, 600/490, 500
See application file for complete search history.

(56) References Cited

U.S. PATENT DOCUMENTS
7,056,291 B2 * 6/2006 Yokozeki et al. ............. 600/485

FOREIGN PATENT DOCUMENTS
JP 2005-261836 9/2005
JP 2006-129958 5/2006

OTHER PUBLICATIONS

Hidehiko Komine et al., "Research and Development of Home-use Evaluation Technique of Degree of . . . ", Japanese Journal of Physical Fitness . . . , Dec. 1, 2005, p. 498, vol. 54.

* cited by examiner

*Primary Examiner* — Michael Kahelin
*Assistant Examiner* — Vasuda Ramachandran
(74) *Attorney, Agent, or Firm* — DLA Piper LLP (US)

(57) ABSTRACT

The present invention is directed to provide an apparatus for measuring a vascular viscoelasticity index which is noninvasive, simple in structure and yet inexpensive.

The present invention provides an apparatus for measuring a vascular viscoelasticity index, which measures a vascular viscoelasticity index $\alpha$ by a formula $\alpha=\{(Pb2-Pa2)-(Pb1-Pa1)\}/(Va2-Va1)$ wherein Pb1 is the maximal value of the first pulse wave; Va1 is the local maximum value of a time derivative value of the first pulse wave; Pa1 is the pulse wave amplitude corresponding to the local maximum value Va1; Pb2 is the maximal value of the second pulse wave; Va2 is the local maximum value of a time derivative value of the second pulse wave; and Pa2 is the pulse wave amplitude corresponding to the local maximum value Va2.

4 Claims, 10 Drawing Sheets

PULSE WAVE

DIFFERENTIAL PULSE WAVE

| MAXIMUM BLOOD PRESSURE : | 135 |
| --- | --- |
| MINIMUM BLOOD PRESSURE : | 80 |
| PULSE : | 62 |
| INDEX α INDICATIVE OF VASCULAR VISCOELASTICITY : | 100 msec |

APPARATUS FOR MEASURING VASCULAR VISCOELASTICITY INDEX

TECHNICAL FIELD

The present invention relates to an apparatus for measuring a vascular viscoelasticity index.

BACKGROUND ART

When the viscoelasticity of a blood vessel is to be measured, the prior art measures the internal pressure and displacement of the blood vessel by use of different means and individually evaluates the viscosity and elasticity of the blood vessel based on the pressure-displacement characteristic (e.g., see the Patent Document 1).

Patent document 1:

Japanese Patent Application Laid-Open (Kokai) No. 2006-129,958

DISCLOSURE OF THE INVENTION

However, the prior art raises a problem in that it requires a large-scaled apparatus for measuring the viscosity and resiliency of a blood vessel since the apparatus requires a device for measuring the internal pressure of the blood vessel and a device for measuring the displacement of the blood vessel.

The prior art also raises another problem in that measuring the viscosity and resiliency of a blood vessel is expensive as a whole since the apparatus requires a device for measuring the internal pressure of the blood vessel and a device for measuring the displacement of the blood vessel.

The present invention is directed to provide an apparatus for measuring a vascular viscoelasticity index which is non-invasive, simple in structure and yet inexpensive.

The present invention provides an apparatus for measuring a vascular viscoelasticity index, which measures a vascular viscoelasticity index a according to the following formula:

$$\alpha = \{(Pb2-Pa2)-(Pb1-Pa1)\}/(Va2-Va1)$$

wherein Pb1 is the maximal value of the first pulse wave; Va1 is the local maximum value of a time differential value of the first pulse wave; Pa1 is the amplitude of the first pulse wave corresponding to the local maximum value Va1; Pb2 is the maximal value of the second pulse wave; Va2 is the local maximum value of a time derivative value of the second pulse wave; and Pa2 is the amplitude of the second pulse wave corresponding to the local maximum value Va2.

In accordance with the present invention, the apparatus for measuring the vascular viscoelasticity index is noninvasive, simple in structure and inexpensive.

EXPLANATION OF REFERENCE NUMERALS

100 . . . Apparatus for measuring a vascular viscoelasticity index;

11 . . . Cuff;

20 . . . CPU;

21 . . . Pulse wave component extraction means;

22 . . . Differentiated waveform forming means;

23 . . . First maximal value detecting means;

24 . . . First local maximum value detecting means;

25 . . . First local maximum value-based amplitude detecting means;

26 . . . Second maximal value detecting means;

27 . . . Second local maximum value detecting means;

28 . . . Second local maximum value-based amplitude detecting means:

29 . . . Index computing means;

Pb1 . . . Maximal value of a first pulse wave component;

Va1 . . . Local maximum value of time derivative pulse wave of the first pulse wave component;

Pa1 . . . First pulse wave amplitude;

Pb2 . . . Maximal value of a second pulse wave component;

Va2 . . . local maximum value of time derivative pulse wave of the second pulse wave component;

Pa2 . . . Second pulse wave amplitude;

$\alpha$ . . . Index representative of a vascular viscoelasticity;

30 . . . ROM;

40 . . . RAM;

50 . . . Operation means;

61 . . . Display means;

62 . . . Printer; and

63 . . . External terminal.

BEST MODE FOR CARRYING OUT THE INVENTION

Best mode for carrying out the present invention is the following embodiments.

First Embodiment

Figure 1:
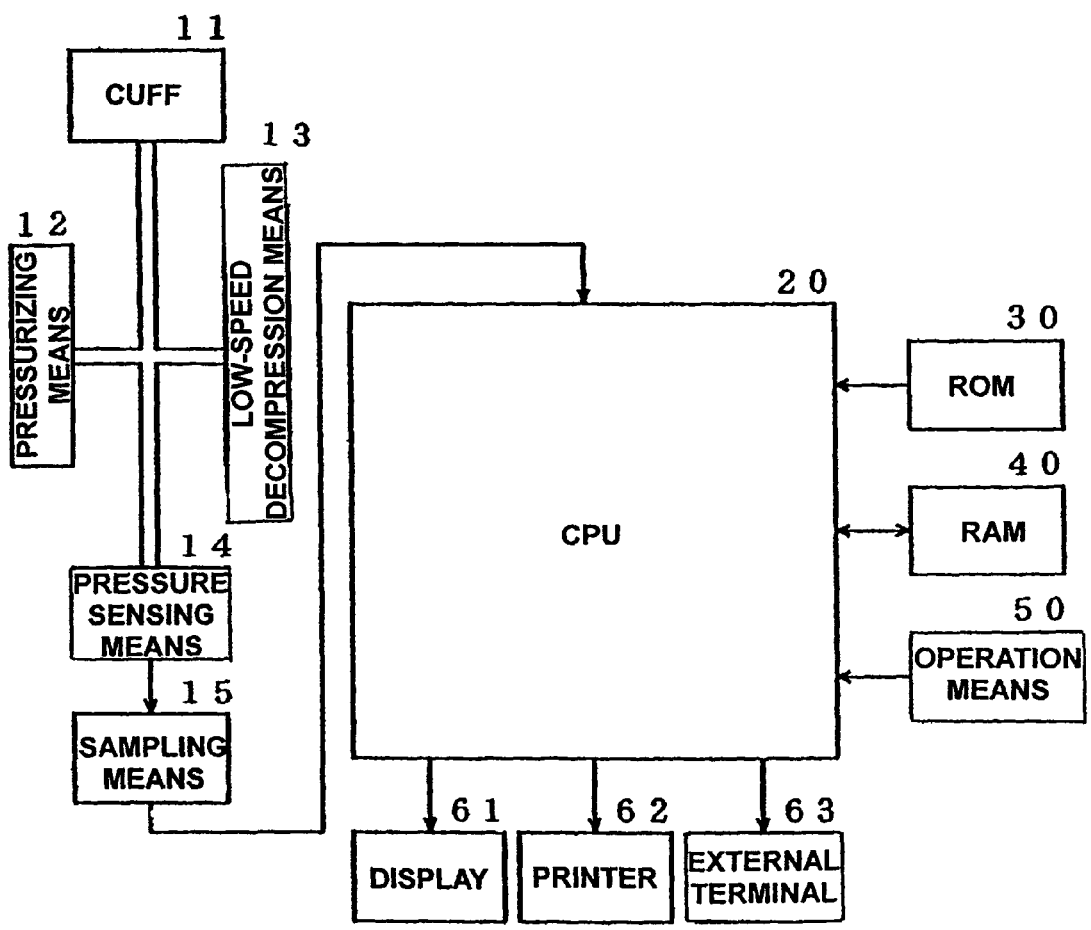
FIG. 1 is a block diagram of an apparatus for measuring a vascular viscoelasticity index 100 according to one embodiment of the present invention.

FIG. 1 is a block diagram of an apparatus for measuring a vascular viscoelasticity index 100 according to one embodiment of the present invention.

The apparatus 100 comprises a cuff 11 to be wound around an arm, wrist, finger, thigh or ankle of a patient, a pressurizing means 12 for pressurizing the cuff 11 to a predetermined pressure which is required to measure a blood pressure, a low-speed decompression means 13 for gradually exhausting the pressure inside the cuff 11 pressurized by the pressurizing means 12, a pressure sensing means 14 that includes a pressure transducer for sensing the pressure in the cuff 11 and is adapted to convert the pressure into an electrical signal (pulse) which is in turn outputted therefrom, a sampling means 15 that counts the electrical signals (pulse) from the pressure sensing means 14 within a predetermined period of time and is adapted to periodically repeat the counting in accordance with a sampling signal and converts the sampled analog value into a digital value, a CPU (Central Processing Unit) 20, a ROM (Read Only Memory) 30, a RAM (Random Access Memory) 40, an operation means 50, a display device 61, a printer 62 and an external terminal 63.

The cuff 11, pressurizing means 12, low-speed decompression means 13 and pressure sensing means 14 are interconnected by a flexible tube. The pressurizing means 12, low-speed decompression means 13, pressure sensing means 14 and sampling means 15 are controlled by the CPU 20.

Figure 2:
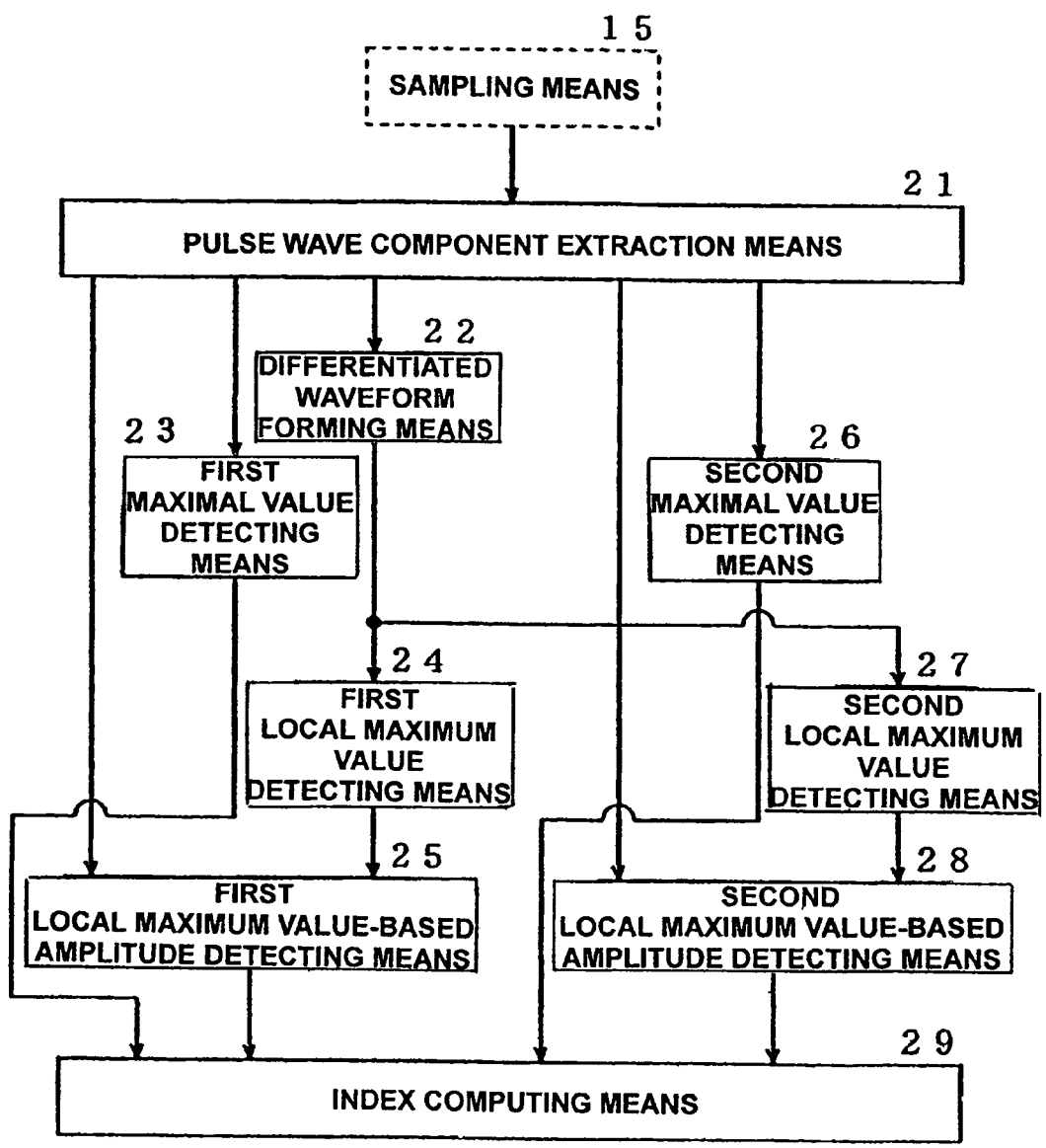
FIG. 2 is a block diagram illustrating the functions of CPU 20.

FIG. 2 is a block diagram illustrating the functions of the CPU 20.

Figure 4:
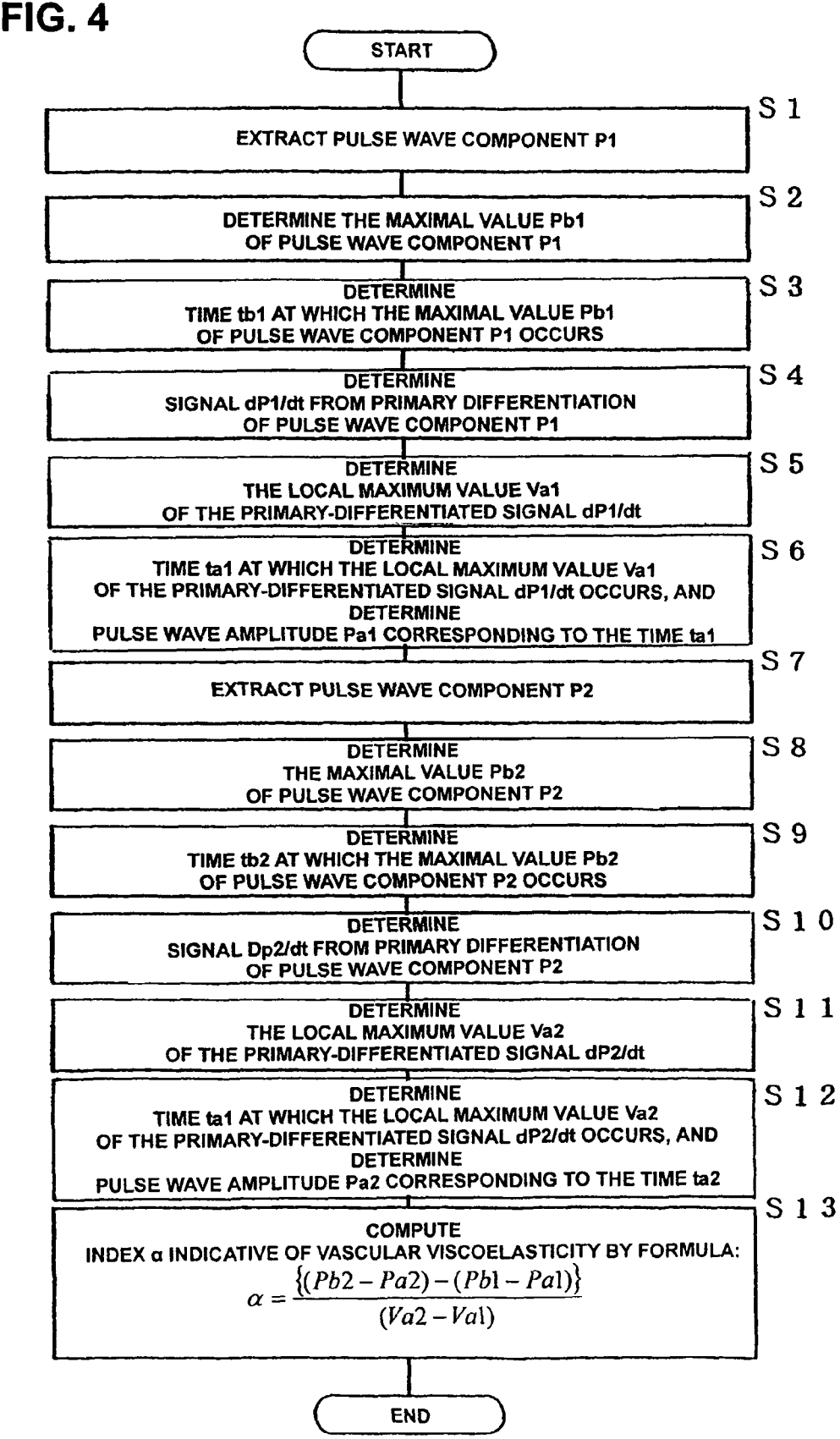
FIG. 4 is a flowchart illustrating the operation of the above embodiment.

The CPU 20 controls the vascular viscoelasticity index measuring apparatus 100 as a whole and functionally cooperates with a program (as shown in FIG. 4), which is stored in the ROM 30, to realize a pulse wave component extraction means 21, a derivative waveform forming means 22, a first maximal value detecting means 23, a first local maximum value detecting means 24, a first local maximum value-based amplitude detecting means 25, a second maximal value detecting means 26, a second local maximum value detecting means 27, a second local maximum value-based amplitude detecting means 28 and an index computing means 29.

The pulse wave component extraction means 21 extracts pulse wave components of the cuff pressure.

The derivative waveform forming means 22 time-differentiates the extracted pulse wave components to calculate primary derivative values on which a derivative waveform is formed. The first maximal value detecting means 23 detects the maximal value Pb1 of a first pulse wave component among a plurality of extracted pulse wave components.

The first local maximum value detecting means 24 detects the local maximum value Va1 of a time derivative pulse wave of the above-described first pulse wave component. The first local maximum value-based amplitude detecting means 25 detects a first pulse wave amplitude value Pa1 which corresponds to the local maximal value Va1 of the time derivative pulse wave of the first pulse wave component.

The second maximal value detecting means 26 detects the maximal value Pb2 of a second pulse wave component among the plurality of extracted pulse wave components, the second pulse wave component being different from the first said pulse wave component. The second local maximum value detecting means 27 detects the local maximum value Va2 of the time derivative pulse wave of the second pulse wave component.

The second local maximum value-based amplitude detecting means 28 detects a second pulse wave amplitude value Pa1 which corresponds to the local maximum value Va1 of the time derivative pulse wave of the first pulse wave component.

The index computing means 29 computes an index α indicative of a vascular viscoelasticity in accordance with the following formula:

$$\alpha = \{(Pb2-Pa2)-(Pb1-Pa1)\}/(Va2-Va1).$$

Since two different pulse waves are used to determine different conditions in which the difference between the internal and external pressures is distinguished from the other, they are not necessarily continuous to each other. Accordingly, two pulse waves used may be different from each other by several beats. Thus, the difference between the maximal value of the first pulse wave and the maximal value of the second pulse wave will be increased. Therefore, even if some noise is mixed, its influence will be reduced. As a result, the index α representative of the vascular viscoelasticity can be more accurately measured.

The ROM 30 is a memory in which a program shown by the flowchart in FIG. 4 is stored. The RAM 40 is a memory for storing the results of computation in the CPU 20. The operation means 50 has conventional function keys and so on.

The operation of the vascular viscoelasticity index measuring apparatus 100 will now be described below.

Figure 3:
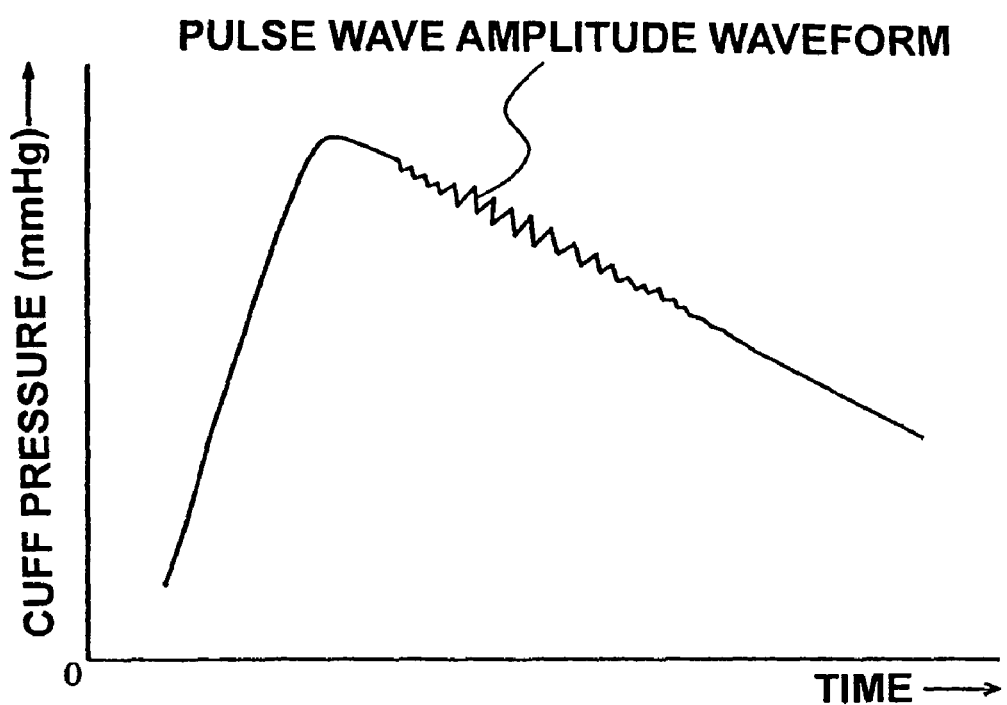
FIG. 3 is a view illustrating a variation in the cuff pressure in the above embodiment.

FIG. 3 illustrates a variation in the cuff pressure in the above embodiment.

The cuff 11 is wound around an arm, wrist or finger with the internal pressure of the cuff 11 being then increased to a predetermined pressure by the pressurizing means 12. Thereafter, the low-speed decompression means 13 substantially linearly decreases the cuff pressure at the ratio of 3-5 mmHg/sec. During this de-pressurization, the pulse wave amplitude components are superimposed over the cuff pressure.

When the vascular viscoelasticity index α is to be computed by the vascular viscoelasticity index measuring apparatus 100, the cuff 11 is first wound around an arm of a patient and a start switch on the operation means 50 is turned on. As a result, the pressurizing means 12 pressurizes the cuff 11 to a pressure that is required to measure the blood pressure. After this pressurization has completed, the low-speed decompression means 13 gradually evacuates the cuff 11. Thus, the pressure change due to the pulse wave components begins to be transmitted to the cuff.

The pressure sensing means 14 converts the changed pressure values of the cuff into electric signals as frequency changes. The sampling means 15 samples the electric signals with a predetermined time interval (e.g., each 5 ms) and outputs pulses corresponding to the sampled cuff pressure values.

FIG. 4 is a flowchart illustrating the operation of the above-described embodiment.

Figure 5:
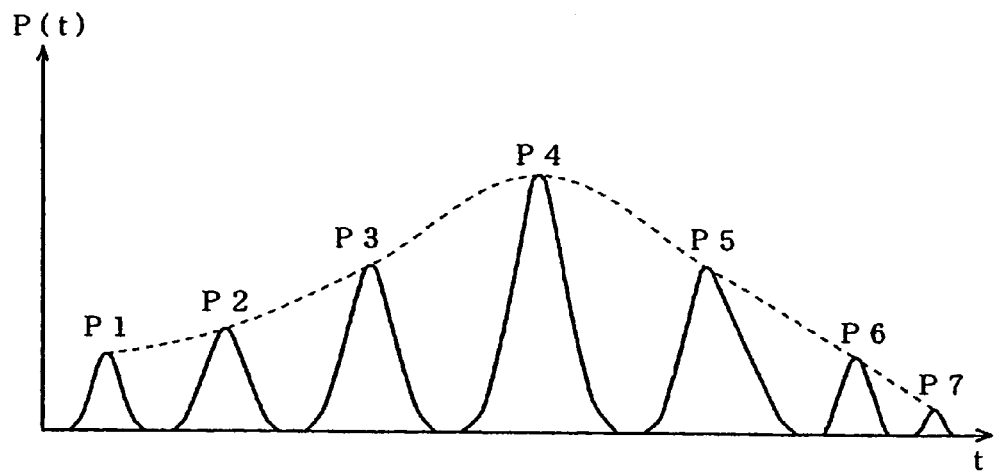
FIG. 5 is a graph showing the pulse wave components P1, P2, . . . , P7 in time series.

FIG. 5 is a graph showing the pulse wave components P1, P2, . . . , P7 in time series.

Pulse waves appear from the vicinity of the maximal blood pressures at each heartbeat as the cuff is depressurized and draw a mountain-shaped or reversed V-shape envelope as shown in FIG. 5. For simplification, FIG. 5 shows only seven pulse waves; however, more than seven pulse waves can be actually measured.

First of all, the pulse wave component P1 will be focused and described. At Step S1, the pulse wave component P1 is extracted by removing depressurization velocity components from the cuff pressure.

Figure 6:
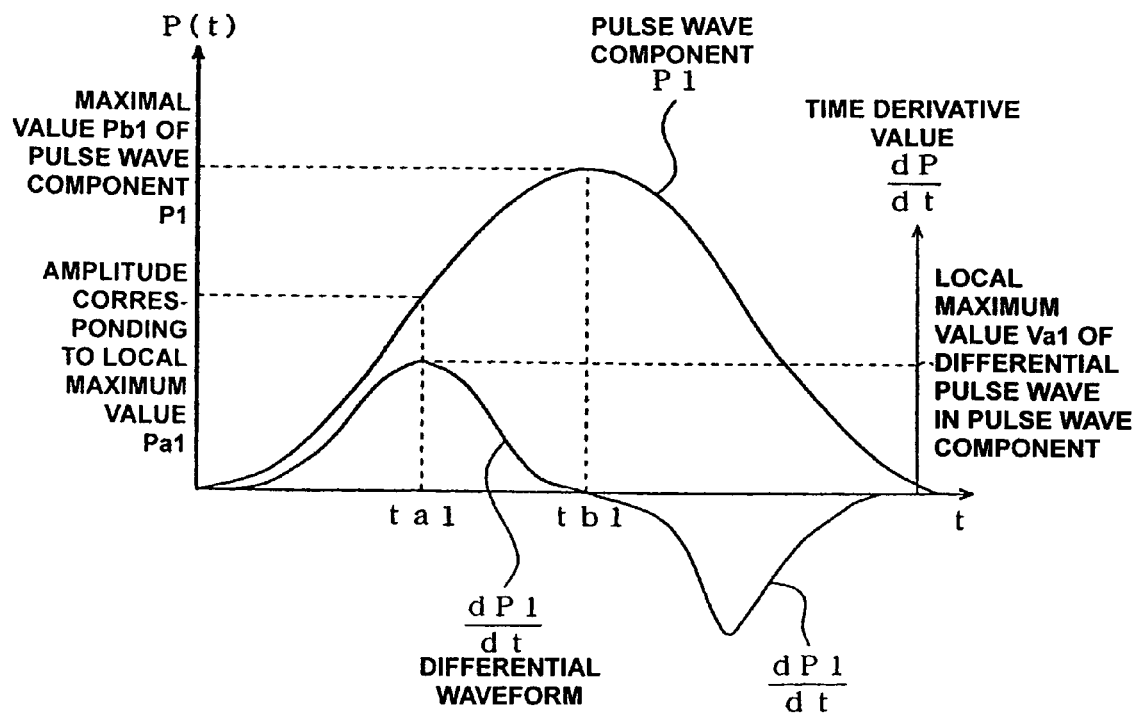
FIG. 6 is a graph showing a pulse wave component P1 extracted at Step S1 in FIG. 5 and a time derivative waveform dP1/dt provided by differentiating the pulse wave component P1 with respect to time.

FIG. 6 is a graph showing a pulse wave component P1 extracted at Step S1 in FIG. 5 and a time derivative waveform dP1/dt provided by differentiating the pulse wave component P1 with respect to time.

At Step S2, the maximal value Pb1 in the pulse wave component P1 is determined. At Step S3, time tb1 at which the maximal value Pb1 in the pulse wave component occurs is determined. At Step S4, a signal dP1/dt provided by primary-differentiating the pulse wave component P1 is determined. At Step S5, the local maximum value Va1 of the primary derivative signal dP1/dt is determined.

At Step S6, time ta1 at which the local maximum value Va1 of the primary derivative signal dP1/dt occurs is determined, and a pulse wave amplitude value Pa1 corresponding to the time ta1 is then determined. In other words, the amplitude value Pa1 corresponding to the local maximum value Va1 is determined. In this regard, (dP/dt)=0 should be noted at the time tb1, as shown in FIG. 6.

Next, the pulse wave component P2 will be focused and described.

Figure 7:
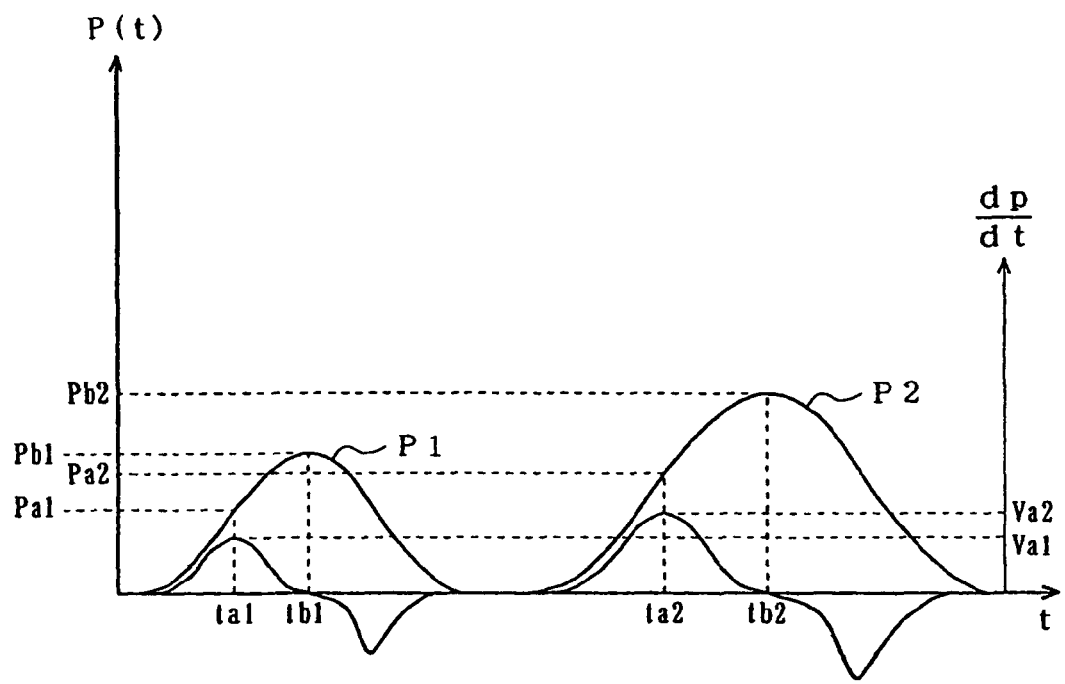
FIG. 7 is a graph showing, in an enlarged scale, pulse wave components P1 and P2 in the above embodiment.

FIG. 7 is a graph showing, in enlarged scale, the pulse wave components P1 and P2 in the above embodiment.

At Step S7, the pulse wave component P2 is extracted by removing depressurization velocity components from the cuff pressure. At Step S8, the maximal value Pb2 in the pulse wave component P2 is determined. At Step S9, time tb2 at which the maximal value Pb2 of the pulse wave component occurs is determined.

At Step S10, a signal dP2/dt provided by primary-differentiating the pulse wave component P2 is determined. At Step S11, the local maximum value Va2 of the primary derivative signal dP2/dt is determined. At Step S12, time ta2 at which the local maximum value Va2 of the primary derivative signal dP2/dt occurs is determined, and a pulse wave amplitude value Pa2 corresponding to the time ta2 is then determined. In other words, the amplitude value Pa2 corresponding to the local maximum value Va2 is determined. In this regard, (dP/dt)=0 should be noted at the time tb2, as shown in FIG. 6.

At Step S13, the index α indicative of the vascular viscoelasticity is computed according to the following formula:

$$\alpha=\{(Pb2-Pa2)-(Pb1-Pa1)\}/(Va2-Va1) \quad (1)$$

Introduction of the above formulas (1) will be described below.

Figure 8:
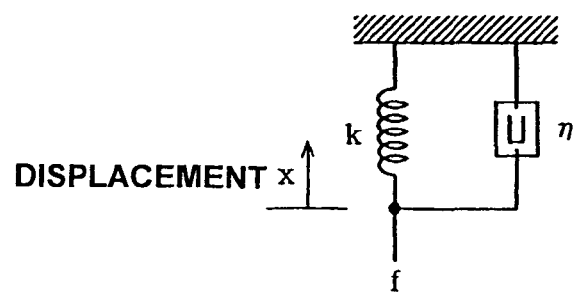
FIG. 8 is a conceptual diagram of Voigt model which is a general viscoelastic model, applied to a vascular viscoelastic model.

A vascular viscoelasticity can be represented as shown in FIG. 8, if Voigt model that is a general viscoelasticity model is applied. If it is assumed here that k is a volume modulus; η is a viscosity resistance; and x is a displacement, then the equation of motion in this system can be represented by the following formula:

$$f=\eta(dx/dt)+kx.$$

If it is assumed that the displacement x is a rate of change in the cuff volume, this rate of volume change is $-\Delta V/V$ wherein $\Delta V$ is a vascular volume change and V is a cuff volume. If it is assumed that the value f is a difference Pt(t) between the internal and external pressures of a blood vessel, the above formula, "$f=\eta(dx/dt)+kx$" can be changed into:

$$Pt(t)=\eta(-\Delta V/V)/dt+k(-\Delta V/V).$$

Actually, the change of volume in the blood vessel can be represented by the change of the cuff pressure. Accordingly, if temperature is constant, it is known that the following relationship:

$$-\Delta V/V=\Delta P/P$$

is established wherein P is a cuff pressure and $\Delta P$ is its change. However, $\Delta V \ll V$.

If it is assumed herein that $P(t)=\Delta P/P$, then $$Pt(t)=\eta(dP/dt)+k\cdot P(t) \quad (2).$$

In this case, η is the viscosity resistance and k is the volume modulus.

Strictly speaking, the cuff also has elasticity and a viscosity. However, they can be ignored if a cuff formed from a material having its elasticity and viscosity sufficiently lower than those of the blood vessel. Accordingly, it is justifiably conceived that η and k are determined by the physical properties of the blood vessel. To calculate the viscosity resistance η and volume modulus k of the blood vessel; however, it is necessary to determine the volume of the blood vessel and the volume of the cuff through distinct means. On the other hand, if the vascular viscoelastic α is to be calculated, its absolute value can be calculated regardless of these volumes.

Since the times tb1 and tb2 at which is the pulse wave P(t) becomes maximum are extremums, (dP/dt)=0.

Consequently, at the times tb1 and tb2, the above formula (2) is as follows:

$$Pt(tb1)=kp(tb1)=k\cdot Pb1 \quad (3)$$

$$Pt(tb2)=kp(tb2)=k\cdot Pb2 \quad (4)$$

If the formula (3) is subtracted from the formula (4), $$Pt(tb2)-Pt(tb1)=k(Pb2-Pb1)$$

Therefore, $$k=\{Pt(tb2)-Pt(tb1)\}/(Pb2-Pb1) \quad (5)$$

Since the numerator of the above formula (5) is equal to the cuff pressure at tb1 minus the cuff pressure at tb2, if it is assumed that the cuff depressurization velocity is $-d(d>0)$, $$Pt(tb2)-Pt(tb1)=d(tb2-tb1)$$

The above formula (5) is converted into the following formula (8):

$$k=d(tb2-tb1)/(Pb2-Pb1) \quad (8)$$

Figure 9:
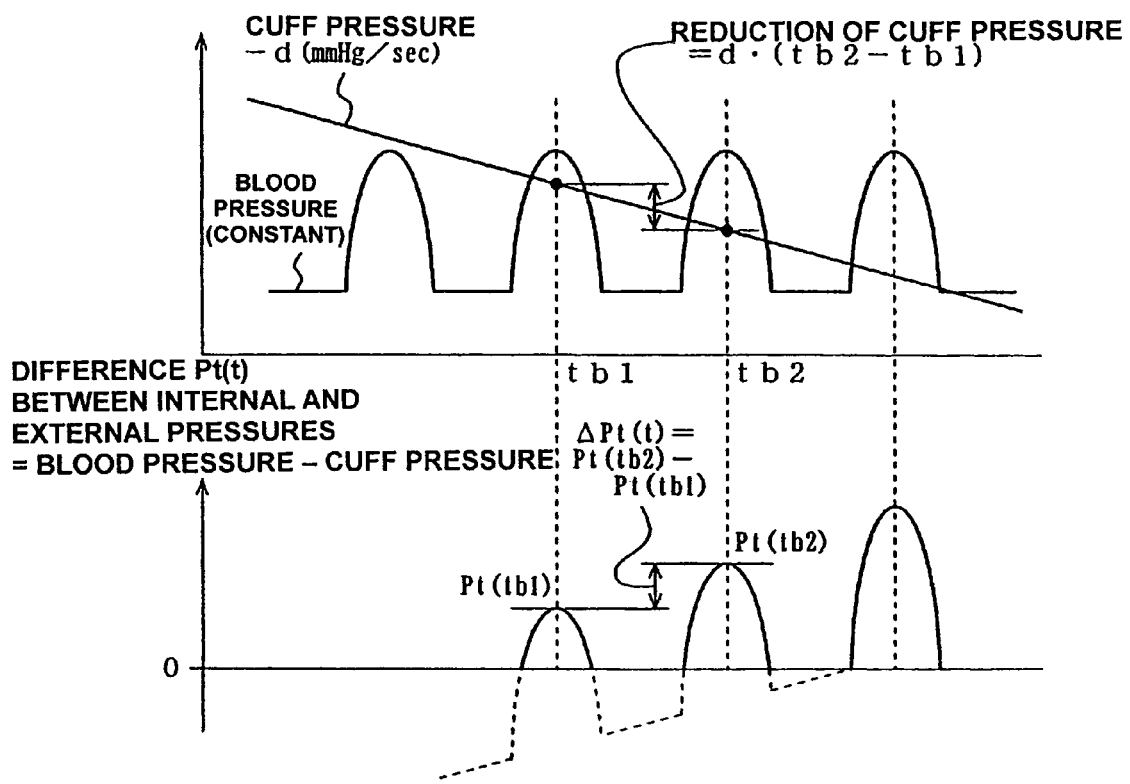
FIG. 9 is a graph showing the fact that a difference Pt(t) between the internal and external pressures of a blood vessel corresponds to a difference between a periodic blood pressure waveform and a linearly lowering cuff pressure.

FIG. 9 is a graph showing the fact that a difference Pt(t) between the internal and external pressures of a blood vessel corresponds to a difference between a periodic blood pressure waveform and a linearly lowering cuff pressure.

Since the difference Pt(t) between the internal and external pressures of the blood vessel corresponds to a difference between a periodic blood pressure waveform and a linearly lowering cuff pressure, if it is assumed that there is no change in the blood pressure, the amount of change $\Delta Pt(t)$ of the Pt(t) becomes equal to the amount of reduction in the cuff pressure.

At the times ta1 and ta2, $$Va1=(dP/dt(t=ta1)), \text{ and}$$

$$Va2=(dP/dt(t=ta2)).$$

Therefore, the following formulas (9) and (10) can be determined from the above formula (2):

$$Pt(ta1)=\eta(dP/dt)+kp(t)=\eta(dP/dt(t=ta1))+kp(ta1)=\eta Va1+kPa1 \quad (9)$$

$$Pt(ta2)=\eta(dP/dt)+kp(t)=\eta(dP/dt(t=ta2))+kp(ta2)=\eta Va2+kPa2 \quad (10).$$

If the above formula (9) is subtracted from the above formula (10), $$Pt(ta2)-Pt(ta1)=\eta(Va2-Va1)+k(Pa2-Pa1) \quad (11)$$

If it is assumed that the depressurization velocity of the cuff is $-d$, the left-hand side: Pt(ta2)−Pt(ta1) in the above formula (11) is substantially equal to d(ta2−ta1).

If this is assigned to the formula (11), $$d(ta2-ta1)\approx\eta(Va2-Va1)+k(Pa2-Pa1)$$

Therefore, $$\eta=\{d(ta2-ta1)-k(Pa2-Pa1)\}/(Va2-Va1) \quad (12)$$

Time difference tb2−tb1 corresponds to pulse cycle, and ta2−ta1 is substantially equal to the pulse cycle. Strictly speaking, however, they may slightly depart from the pulse cycle. If the departing is sufficiently smaller in comparison with the pulse cycle, it can be considered that tb2−tb1=ta2−ta1=pulse cycle. Therefore, the above formula (12) can be established.

If k=d(Pb2−Pb1)/(tb2−tb1) shown in the formula (8) is assigned to k of the above formula (12), $$\eta=\{d(ta2-ta1)-k(Pa2-Pa1)\}/(Va2-Va1)=\{d(ta2-ta1)-d(tb2-tb1)/(Pb2-Pb1)(Pa2-Pa1)\}/(Va2-Va1)=d\{(ta2-ta1)(Pb2-Pb1)-(tb2-tb1)(Pa2-Pa1)\}/\{(Pb2-Pb1)(Va2-Va1)\} \quad (14)$$

At Step S13, the index α representative of the vascular viscoelasticity is computed as described above.

If it is assumed that α=η/k, the Voigt model can be represented by:

$$f=\eta(dx/dt)+kx$$

wherein x is a displacement of an elastic body. In the above, α(=η/k) is referred to as a delay time, and it is an important index in the rheology.

If the above formulas (6) and (14) are assigned to the above formula, α=η/k, then $$\alpha=\eta/k=[d\{(ta2-ta1)(Pb2-Pb1)-(tb2-tb1)(Pa2-Pa1)\}/\{(Pb2-Pb1)(Va2-Va1)\}]/\{d(tb2-tb1)/(Pb2-Pb1)\}=\{(ta2-ta1)(Pb2-Pb1)-(tb2-tb1)(Pa2-Pa1)\}/\{(tb2-tb1)(Va2-Va1)\}$$

That is to say, the following formula (15) is established:

$$\alpha=\{(ta2-ta1)(Pb2-Pb1)-(tb2-tb1)(Pa2-Pa1)\}/\{(tb2-tb1)(Va2-Va1)\} \quad (15)$$

Time difference tb2−tb1 corresponds to the pulse cycle, and ta2−ta1 is a value substantially equal to the pulse cycle. Strictly speaking, they may slightly depart from the pulse cycle. However, if the departing is sufficiently smaller in comparison with the pulse cycle, it can be considered that tb2−tb1=ta2−ta1=pulse cycle. Thus, the formula (15) becomes the following formula (16):

$$\alpha=\{(Pb2-Pb1)-(Pa2-Pa1)\}/(Va2-Va1)=\{(Pb2-Pa2)-(Pb1-Pa1)\}/(Va2-Va1) \quad (16)$$

In the above formula, the index α is a time constant indicative of a vascular viscoelastic property and is an important index for arteriosclerosis.

The index α is represented by second(s). According to this method, the index α is an objective one that is not influenced by the dispersion of cuff capacity and vascular volume and the individual difference.

In this regard, η/k=α is referred to "delay time" or "relaxation time" in the rheology.

Figure 10:
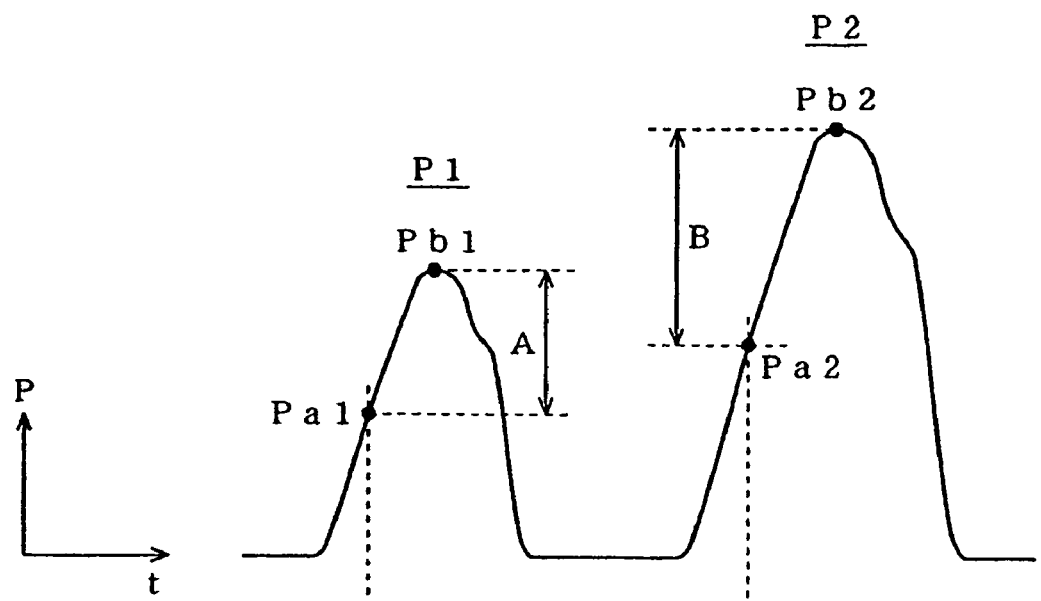
FIG. 10 is a graph illustrating an index a representing the vascular viscoelasticity of a blood vessel associated with the pulse wave components P1 and P2 of FIG. 7 in a different manner.
Figure 10:
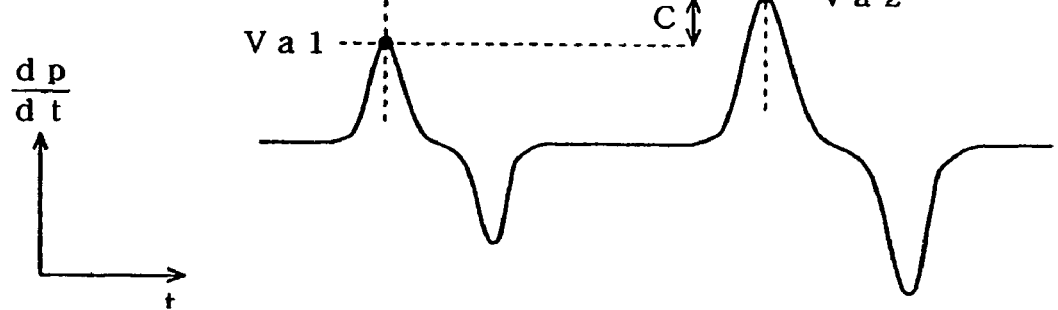

FIG. 10 is a graph illustrating an index α representing the vascular viscoelasticity of a blood vessel associated with the pulse wave components P1 and P2 of FIG. 7 in a different manner.

If it is assumed that A=(Pb1−Pa1); B=(Pb2−Pa2); and C=(Va2−Va1) as shown in FIG. 10, then the following formula (17) is established:

$$\alpha=(B-A)/C=\eta/k \quad (17)$$

The index α indicative of the vascular viscoelasticity is α=(B−A)/C=η/k, as shown in the above formula (17). The index α is increased as C is reduced and (B−A) is increased.

The unit of the index α is second. Usually, the index α ranges from about 20 msec to about 200 msec.

Figure 11:
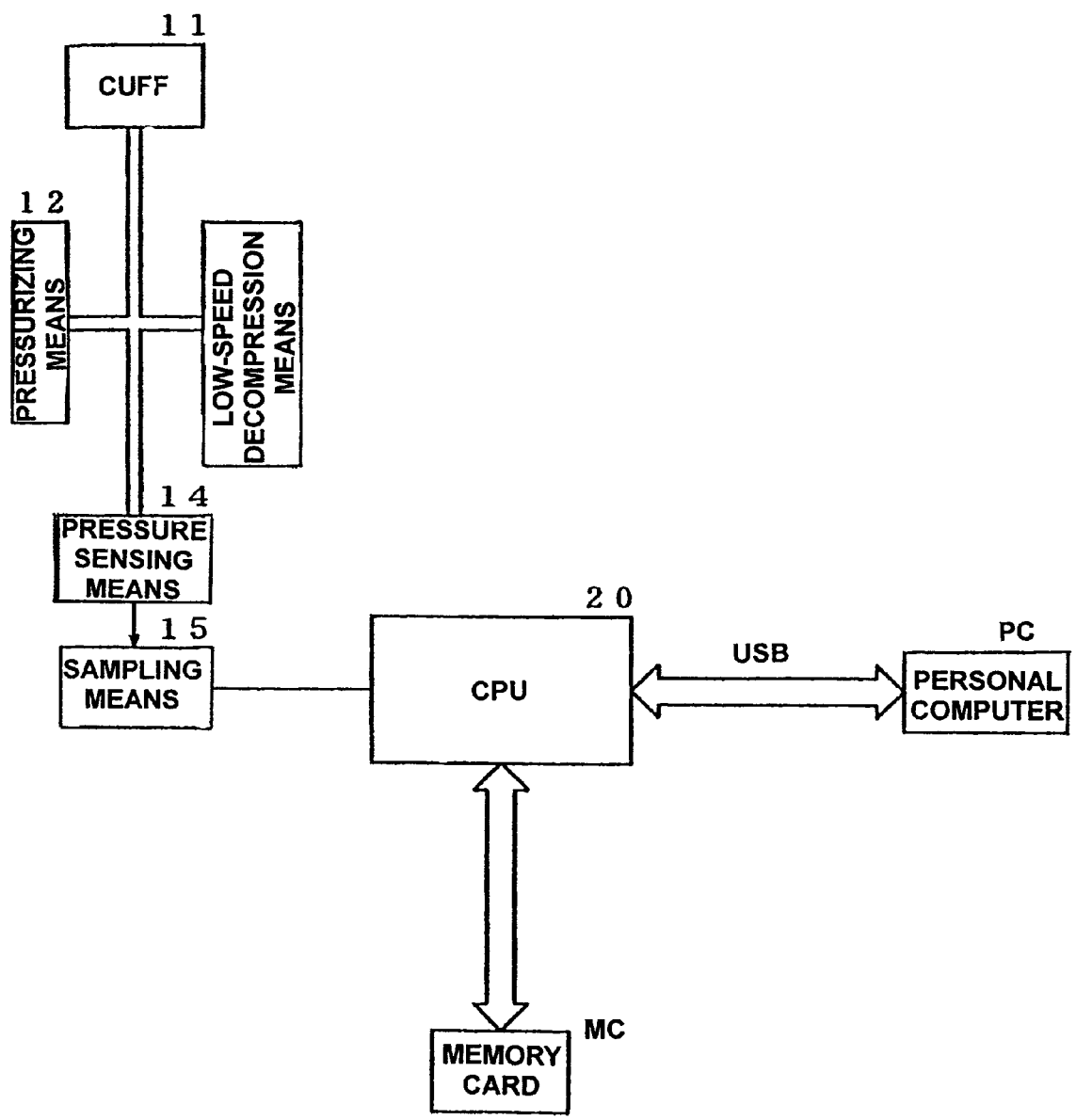
FIG. 11 is a block diagram similar to FIG. 1, but illustrating concrete examples of an external output and internal memory.

FIG. 11 is a block diagram similar to FIG. 1, illustrating concrete examples of an external output and internal memory.

The CPU 20 is an example in which the index α representative of the vascular viscoelasticity is outputted toward a personal computer PC and a memory card MC. In other words, the CPU 20 exemplifies a computation result output means for externally outputting the index α indicative of the vascular viscoelasticity.

Figures 12, 13:
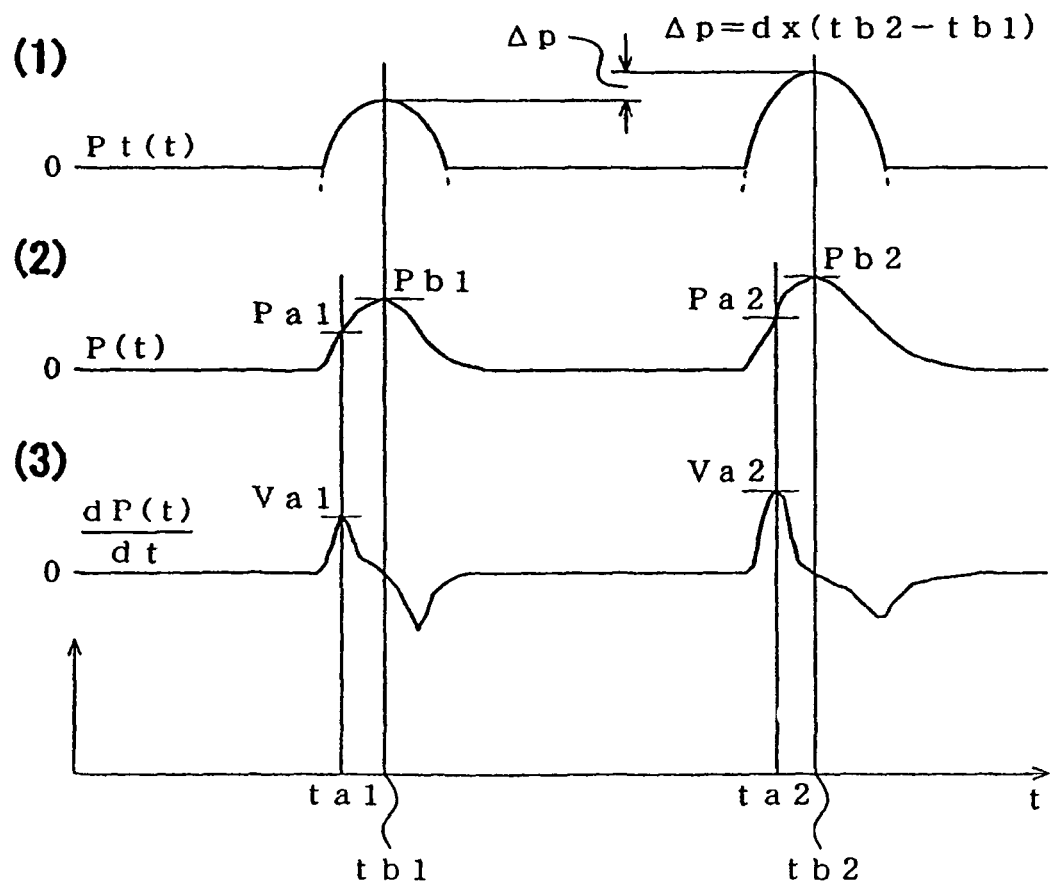
FIG. 12 is data including the index $\alpha$ representative of the vascular viscoelasticity sent to and displayed on a personal computer PC in the embodiment of FIG. 11.
FIG. 13 is a time chart illustrating the volume elasticity k and vascular viscosity resistance $\eta$ determined in the embodiment of FIG. 11.

FIG. 12 is data including the index α representative of the vascular viscoelasticity sent to and displayed on a personal computer PC in the embodiment of FIG. 11.

FIG. 13 is a time chart illustrating the volume elasticity k and vascular viscosity resistance η determined in the embodiment of FIG. 11.

In FIG. 13, (1) is a graph showing a difference Pt(t) between the internal and external pressures of a blood vessel; (2) is a graph showing a pulse wave component P (t); and (3) is a graph showing a time derivative waveform (dP/dt).

The volume modulus k is represented by the following formula:

$$k=d(tb2-tb1)/(Pb2-Pb1) \quad (18)$$

The viscosity resistance η is represented by the following formula:

$$\eta=d\{(ta2-ta1)(Pb2-Pb1)-(tb2-tb1)(Pa2-Pa1)\}/\{(Pb2-Pb1)(Va2-Va1)\} \quad (19)$$

The above embodiment can quantitatively express the viscosity and resiliency of a blood vessel in an apparatus that measures vascular viscoelasticity index.

Further, the above embodiment also provides a method for quantitatively measuring the viscoelasticity of a blood vessel as time constant, and since this method uses a measurement algorithm that is feasible in the hardware of the most general electronic hemonamometer, its structure is simple.

Moreover, the above embodiment can produce an apparatus for measuring a vascular viscoelasticity index using the hardware of the conventional oscillometric hemomanometer. Therefore, the above embodiment can extremely inexpensively provide an apparatus for measuring a vascular viscoelasticity index.

Further, the above embodiment is extremely safe in theory and can be very advantageous for arteriosclerosis prevention.

Still further, the above embodiment can measure the vascular viscoelasticity regardless of the cuff capacity and the vascular thickness.

Additionally, the above embodiment can measure the vascular viscoelasticity of a patient when measuring the blood pressure without making special preparations.

More additionally, the above embodiment may measure the blood pressure while at the same time measuring the vascular viscoelasticity, and also may average data for several pulse beats.

Thus, errors due to the physiologic fluctuation of pulsatile flow can be reduced.

The invention claimed is:

1. An apparatus for measuring a vascular viscoelasticity index, characterized in that the apparatus comprises:
   a pulse wave component extraction means for extracting pulse wave components of a cuff pressure;
   a derivative waveform forming means for time-differentiating the extracted pulse wave components to calculate primary derivative values on which a derivative waveform is formed;
   a first maximal value detecting means for detecting a maximal value Pb1 of a first pulse wave component among a plurality of extracted pulse wave components;
   a first local maximum value detecting means for detecting a local maximum value Va1 of a time derivative pulse wave of said first pulse wave component;
   a first local maximum value-based amplitude detecting means for detecting a first pulse wave amplitude value Pa1 which corresponds to the local maximal value Va1 of the time derivative pulse wave of said first pulse wave component;

a second maximal value detecting means for detecting a maximal value Pb2 of a second pulse wave component among the plurality of extracted pulse wave components, the second pulse wave component being different from the first said pulse wave component;

a second local maximum value detecting means for detecting a local maximum value Va2 of a time derivative pulse wave of said second pulse wave component;

a second local maximum value-based amplitude detecting means for detecting a second pulse wave amplitude value Pa2 which corresponds to the local maximal value Va2 of the time derivative pulse wave of said second pulse wave component; and an index computing means for computing an index $\alpha$ indicative of a vascular viscoelasticity by a formula $\alpha=\{(Pb2-Pa2)-(Pb1-Pa1)\}/(Va2-Va1)$.

2. The apparatus as defined in claim 1, characterized in that said first and second pulse wave components are pulse wave components provided by one of a cuff depressurization means and a cuff pressurizing means.

3. The apparatus as defined in claim 1, characterized in that said first and second pulse wave components are different from each other by at least one beat.

4. The apparatus as defined in claim 1, characterized in that the apparatus further comprises at least one of: a display means for displaying the index $\alpha$ indicative of said computed vascular viscoelasticity; an output means for externally outputting the index $\alpha$ indicative of said computed vascular viscoelasticity; and a storage control means for permitting a memory within said apparatus to store the index $\alpha$ indicative of said computed vascular viscoelasticity.

* * * * *

UNITED STATES PATENT AND TRADEMARK OFFICE
CERTIFICATE OF CORRECTION

| | | |
|---|---|---|
| PATENT NO. | : 8,251,910 B2 | Page 1 of 1 |
| APPLICATION NO. | : 12/309843 | |
| DATED | : August 28, 2012 | |
| INVENTOR(S) | : Yukiyoshi Saito | |

It is certified that error appears in the above-identified patent and that said Letters Patent is hereby corrected as shown below:

On The Title Page, Item (22) PCT filed date should read:
- Jul. 27, 2007

Signed and Sealed this
Seventh Day of June, 2016

Michelle K. Lee
*Director of the United States Patent and Trademark Office*